(12) United States Patent
Fukui

(10) Patent No.: US 8,205,482 B2
(45) Date of Patent: Jun. 26, 2012

(54) HYDROGEN SENSOR WITH DETECTION FILM COMPRISED OF RARE EARTH METAL PARTICLES DISPERSED IN A CERAMIC

(75) Inventor: Katsuhiko Fukui, Iwate (JP)

(73) Assignee: Mikuni Corporation, Tokyo (JP)

( * ) Notice: Subject to any disclaimer, the term of this patent is extended or adjusted under 35 U.S.C. 154(b) by 556 days.

(21) Appl. No.: 12/521,234

(22) PCT Filed: Dec. 28, 2007

(86) PCT No.: PCT/JP2007/075261
§ 371 (c)(1),
(2), (4) Date: Jun. 25, 2009

(87) PCT Pub. No.: WO2008/081921
PCT Pub. Date: Jul. 10, 2008

(65) Prior Publication Data
US 2010/0089123 A1   Apr. 15, 2010

(30) Foreign Application Priority Data

Dec. 28, 2006   (JP) .................................. 2006-356334

(51) Int. Cl.
*G01N 7/00* (2006.01)
(52) U.S. Cl. ........................................... 73/31.05
(58) Field of Classification Search ................ 73/31.05, 73/31.06; 422/88
See application file for complete search history.

(56) References Cited

U.S. PATENT DOCUMENTS

| | | | | |
|---|---|---|---|---|
| 6,006,582 A | * | 12/1999 | Bhandari et al. | 73/23.2 |
| 6,265,222 B1 | * | 7/2001 | DiMeo et al. | 436/144 |
| 6,463,789 B2 | * | 10/2002 | Moos et al. | 73/31.06 |
| 6,562,747 B2 | * | 5/2003 | Symons et al. | 501/103 |
| 6,596,236 B2 | * | 7/2003 | DiMeo et al. | 422/88 |
| 7,416,702 B2 | * | 8/2008 | Yamaguchi et al. | 422/88 |
| 8,025,843 B2 | * | 9/2011 | Ono et al. | 422/88 |
| 2002/0017126 A1 | * | 2/2002 | DiMeo et al. | 73/31.05 |
| 2002/0102347 A1 | * | 8/2002 | Clyde et al. | 427/58 |
| 2002/0108872 A1 | * | 8/2002 | Symons et al. | 205/784 |
| 2003/0153088 A1 | * | 8/2003 | DiMeo et al. | 436/113 |

(Continued)

FOREIGN PATENT DOCUMENTS

JP   57-80550 A   5/1982

(Continued)

OTHER PUBLICATIONS

English Language Abstract for JP2005-274559.
English Language Abstract for JP62-222153.
English Language Abstract for JP57-80550.
English Language Abstract for JP2002-535651.

*Primary Examiner* — Hezron E Williams
*Assistant Examiner* — Nathaniel Kolb
(74) *Attorney, Agent, or Firm* — Norris McLaughlin & Marcus P.A.

(57) ABSTRACT

A hydrogen sensor (100) is provided with a substrate (2), a detection film (4) formed on the substrate (2), and a hydrogen permeable protective film (10) formed on the detection film (4). The detection film (4) is composed of a first ceramic (6) and rare-earth metal particles (8) dispersed in the first ceramic (6). The protective film (10) is composed of a second ceramic (12) and hydrogen permeable metal particles (14) dispersed in the second ceramic (12). Preferably, the thickness of the detection film (4) is 5 to 1,000 nm, and the thickness of the hydrogen permeable protective film (10) is 5 to 40 nm.

16 Claims, 9 Drawing Sheets

U.S. PATENT DOCUMENTS

| | | | |
|---|---|---|---|
| 2004/0093928 A1* | 5/2004 | DiMeo et al. | 73/23.2 |
| 2004/0131865 A1* | 7/2004 | Kim et al. | 428/433 |
| 2004/0180203 A1* | 9/2004 | Yadav et al. | 428/402 |
| 2005/0188845 A1* | 9/2005 | Yamaguchi et al. | 96/11 |
| 2005/0189223 A1* | 9/2005 | Yamaguchi et al. | 204/431 |
| 2005/0214170 A1* | 9/2005 | Kading | 422/88 |
| 2009/0090626 A1* | 4/2009 | Holt et al. | 204/431 |

FOREIGN PATENT DOCUMENTS

| | | |
|---|---|---|
| JP | 62-222153 A | 9/1987 |
| JP | 2002-535651 A | 10/2002 |
| JP | 2005-274559 A | 10/2005 |

\* cited by examiner

HYDROGEN SENSOR WITH DETECTION FILM COMPRISED OF RARE EARTH METAL PARTICLES DISPERSED IN A CERAMIC

TECHNICAL FIELD

The present invention relates to a hydrogen sensor and a method for manufacturing the same. More particularly, the present invention relates to a hydrogen sensor and a method for manufacturing the same suitable for detecting comparatively low concentration hydrogen gas leaking from various types of equipment that handle hydrogen such as automotive fuel cells and household fuel cells, or suitable for detecting comparatively high concentration hydrogen gas in equipment that handles hydrogen gas.

BACKGROUND ART

Demand for hydrogen is expected to increase rapidly in all industrial fields. Within this context, hydrogen sensors for detecting low concentration hydrogen gas leaks or for measuring the concentration of hydrogen gas are under development.

Various sensors for detecting hydrogen gas has been proposed in the past. For example, there has been a proposal (Patent Literature 1) for a sensor that takes a rare earth metal thin film such as yttrium (Y) or lanthanum (La) as a hydrogen detection film.

This sensor utilizes the fact that when the rare earth metal composing the detection film is exposed to hydrogen, the physical properties change. In this proposal, the physical change in this detection film is detected, and that change is utilized to detect hydrogen. The rare earth metal composing the detection film is adversely influenced by non-hydrogen components such as nitrogen, oxygen, ammonia, or hydrocarbons present together with the hydrogen. This sensor covers the surface of the rare earth metal film with a hydrogen permeable protective film composed of hydrogen permeable palladium (Pd), platinum (Pt) or an alloy of these in order to avoid the adverse influence of the non-hydrogen components.

Nonetheless, the volume of the hydrogen permeable metals such as Pd and Pt repeatedly expand and contract when absorbing and releasing hydrogen. The mechanical stress induced by this expansion and contraction causes deterioration and cracking of the hydrogen permeable metal film over time. For that reason, hydrogen sensors using a hydrogen permeable metal film as a protective layer have poor durability.

The hydrogen permeable metals like Pd and Pt are prone to diffuse into rare earth metals such as yttrium (Y) and Lanthanum (La). When this diffusion occurs, the hydrogen detection capacity of the detection film composed of rare earth metals decreases over time. Consequently, hydrogen sensors using the aforementioned hydrogen permeable metals in the protective film have durability issues.

Moreover, because Pd and Pt are extremely expensive metals, hydrogen sensors that use these metals in the protective film have high manufacturing costs.

In order to resolve the aforementioned problems, a hydrogen sensor using a protective film in which hydrogen permeable metal particles are dispersed in a ceramic material was proposed (Patent Literature 2). This protective film has hydrogen permeable palladium (Pd), platinum (Pt), niobium (Nb), vanadium (V), tantalum (Ta) particles or alloy particles of these dispersed into a ceramic composed of nitrides or oxides of aluminum (Al) and/or silicon (Si), or of silicides of rare earth elements.

In this hydrogen sensor as well, volume changes of the detection film in association with the lattice state when hydrogenating and dehydrogenating cause repeated stress to the protective film. As a result, the protective film may be damaged. In order to prevent damage to this protective film, the thicknesses of the detection film and the protective film are adjusted. However, this method restricts the degrees of freedom in terms of designing the sensor specifications. For example, if the thickness of the detection film is increased, it is necessary to make the protective film thicker as well. In this case however, the problem emerges that the sensor response speed is slowed.

Further, oxygen and water vapor may permeate the protective film through pinholes that may be present in the protective film or through film defects caused by impurities included in the protective film. In such a case, these harmful non-hydrogen gases alter the detection film, and it is necessary to make a thick protective film in order to prevent alteration.

Lamination of 2 layers of protective film onto the detection film was proposed in Patent Literature 2 as a method to resolve this problem. This method is effective for resolving the aforementioned problems. However, the problem of increased manufacturing steps then arises.

For these reasons, it is desirable to develop a low cost hydrogen sensor with excellent durability.

Patent Literature 1: National Publication of Translated Version No. 2002-535651 (Claims)

Patent Literature 2: Japanese Patent Application Laid-open No. 2005-274559 (Claims)

DISCLOSURE OF THE INVENTION

Technical Problem

As a result of assiduous study to resolve the aforementioned problems, the present inventors conceived of a detection film which rare earth metal particles are dispersed in ceramic. According to the structure of this detection film, hydrogenation and dehydrogenation of rare earth particles occurs during hydrogen detection, but the protective film is not distorted because the highly rigid ceramic absorbs the volume change associated with this hydrogenation and dehydrogenation based on the lattice transformation of the rare earth metal particles. The present invention was perfected based on the aforementioned discovery, and an object is to provide a hydrogen sensor and manufacturing method of the same that can resolve the aforementioned problems.

The present invention achieves the aforementioned object, and is described below.

[1] A hydrogen sensor a substrate, a detection film formed on the aforementioned substrate, and a hydrogen permeable protective film formed on the aforementioned detection film, wherein the aforementioned detection film comprises a first ceramic and rare earth metal particles dispersed in the aforementioned first ceramic, and the aforementioned protective film comprises a second ceramic and hydrogen permeable metal particles dispersed is the aforementioned second ceramic.

[2] The hydrogen sensor according to [1], wherein the thickness of the detection film is 5 to 1000 nm, and the thickness of the hydrogen permeable protective film is 5 to 40 nm.

[3] The hydrogen sensor according to [1], wherein the detection film contains 30 to 80 mass % rare earth metal particles.

[4] The hydrogen sensor according to [1], wherein the rare earth metal particles are formed of at least one selected from the group consisting of yttrium (Y), cerium (Ce) and lanthanum (La).

[5] The hydrogen sensor according to [1], wherein the rare earth metal particles are amorphous particles and/or rod-shaped particles.

[6] The hydrogen sensor according to [1], wherein the first ceramic of the detection film is formed of a nitride or oxide of group IVa, Va or VIa metal elements.

[7] The hydrogen sensor according to [1], wherein the content percentage of the hydrogen permeable metal particles in the hydrogen permeable protective film is 20 to 70 mass %.

[8] The hydrogen sensor according to [1], wherein the hydrogen permeable metal particles are amorphous particles and/or rod-shaped particles.

[9] The hydrogen sensor according to [1], wherein the hydrogen permeable metal particles are at least one selected from the group consisting of palladium (Pd), platinum (Pt), niobium (Nb), vanadium (V), tantalum (Ta) and alloys of these.

[10] The hydrogen sensor according to [1], wherein the second ceramic of the hydrogen permeable protective film is formed of a nitride or oxide of group IVa, Va or VIa metal elements.

[11] The hydrogen sensor according to [1], wherein the ceramics forming the detection film and the hydrogen permeable protective film are formed of the same materials.

[12] The hydrogen sensor according to [1], wherein the substrate is a glass plate or a ceramic plate.

[13] The hydrogen sensor according to [1], wherein a heater is provided on the substrate.

[14] The hydrogen sensor according to [12], wherein the heater is a resistance film which is formed on one surface of the substrate and formed of platinum, ruthenium oxide or silver-palladium alloy film.

[15] A method for manufacturing the hydrogen sensor described in [1], wherein a detection film in which rare earth metal particles are dispersed in a first ceramic is formed by conducting vapor phase epitaxy or sputtering of a rare earth metal and the first ceramic material simultaneously onto one side of a substrate, and then a protective film in which hydrogen permeable metal particles are dispersed in a second ceramic is formed by conducting vapor phase epitaxy or sputtering of a hydrogen permeable metal and the second ceramic material simultaneously onto the detection film.

[16] The method for manufacturing the hydrogen sensor according to [15], wherein the rare earth metal particles and/or hydrogen permeable metal particles are amorphous particles and/or rod-shaped particles.

Advantageous Effects

The rare earth metal particles of the detection film used in the hydrogen sensor of the present invention hydrogenate and dehydrogenate when detecting hydrogen, but the highly rigid ceramic absorbs the volume change associated with this hydrogenation and dehydrogenation based on lattice transformation of the rare earth metal particles. As a result, volume change of the detection film is suppressed. Consequently, destruction of the protective film caused by volume change of the detection film can be prevented.

Because the rare earth metal particles in the detection film are dispersed in ceramic, the surfaces of the majority of rare earth metal particles are not directly exposed to the outside. Consequently, even if there are defects such as micro-pinholes in the protective film, adverse gases do not penetrate from the outside through these, and only a very small part of the rare earth metal particles deteriorate, with no overall deterioration. As a result, sensor durability is heightened. Further, because a thin protective film can be made, the sensor response speed is heightened. Moreover, because a thin protective film can be made, use amount of hydrogen permeable metal can be suppressed. Accordingly, the hydrogen sensor can be manufactured at low cost.

The hydrogen permeable metal particles of the protective film of the hydrogen sensor of the present invention are dispersed roughly evenly in the ceramic material. The highly rigid ceramic material receives the increase and decrease of volume of the hydrogen permeable metal particles when the hydrogen permeable metal particles are absorbing and releasing hydrogen, and the ceramic material accommodates the mechanical stress produced. As a result, there is little deterioration of the hydrogen permeable metal by hydrogenation, and the durability of the protective film is improved.

The protective film used in the hydrogen sensor of the present invention has excellent hydrogen gas permeability. However, gases other than hydrogen, for example, gases such as nitrogen and oxygen, cannot permeate this protective film. The protective film selectively allows hydrogen gas contained within mixed gas to pass through and be provided to the detection film. For that reason, the present sensor is highly selective for hydrogen gas.

The protective film of the hydrogen sensor of the present invention does not allow non-hydrogen gases such as nitrogen, oxygen and hydrocarbons to permeate, and therefore a decrease in the sensor performance of the detection film caused by non-hydrogen gases is prevented.

Further, because the protective film and detection film of hydrogen sensor of the present invention are configured by ceramic in which metal particles are dispersed, the hydrogen permeable metal particles in the protective film have little contact with the rare earth metal particles in the detection film. For that reason, diffusion of the hydrogen permeable metal particles into the rare earth metal can be reduced. As a result, the reduction of performance over time that this diffusion causes in the hydrogen sensor of the detection film can be prevented.

Figure 1:
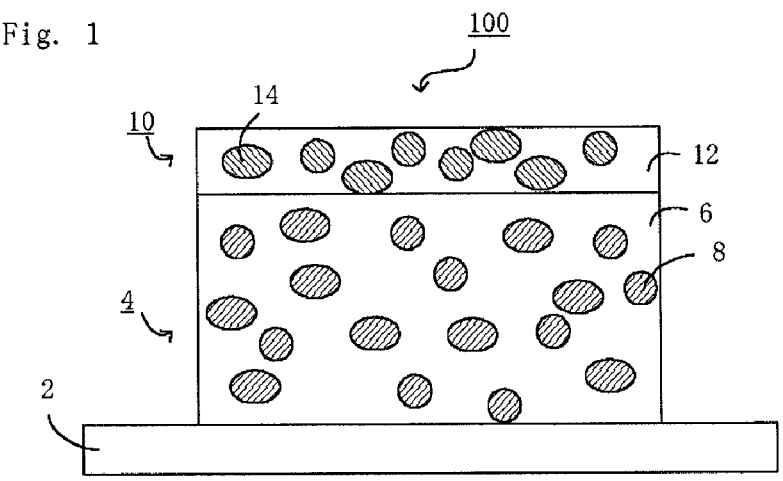
FIG. 1 is a cross-sectional diagram indicating one example of the hydrogen sensor of the present invention.

EXPLANATION OF REFERENCE 100, 200, 300, 400 Hydrogen sensor
2, 32, 52, 131 Substrate
4, 34, 54, 136 Detection film
6 First ceramic
8, 38 Rare earth metal particles
10, 40, 60, 137 Protective film
12 Second ceramic
14, 44, 64a, 64b Hydrogen permeable metal particles
58a Rod-shaped rare earth metal particles
58b Spherical rare earth metal particles
132a, 132b Element electrode
133 Heater
134a, 134b Heater electrode
135a, 135b Wire
141 Filter
142 Cap
143 Pin
144 Plate
145 Grommet
146 Cord
147 Connector

BEST MODE FOR CARRYING OUT THE INVENTION

The present invention will be explained in detail below while referring to the diagrams.

FIG. 1 is a conceptual diagram indicating one example of the hydrogen sensor of the present invention. In FIG. 1, 100 is a hydrogen sensor, and 2 is a substrate.

(Substrate)

Substrate 2 is preferably airtight, insulative and heat-resistant flat plate. Examples of the material of the substrate include glass plate, alumina ceramic, sapphire, quartz monocrystal, silicon, and silicon nitride ceramic.

(Detection Film)

A detection film 4 is formed on the upper surface of the substrate 2. This detection film 4 is composed of a first ceramic 6, and multiple rare earth metal microparticles 8 dispersed inside of the first ceramic 6. The rare earth metal particles 8 hydrogenate by absorbing hydrogen, and dehydrogenate by releasing hydrogen. At that time, the resistance value of the rare earth metal particles 8 changes. Hydrogen can be detected by measuring the changes in this resistance. The detection film 4 takes the first ceramic 6 as a matrix, and the multiple rare earth metal particles 8 are roughly uniformly dispersed therein.

The thickness of the detection film 4 is preferably 5 to 1000 nm, more preferably 30 to 100 nm. If the thickness of the detection film 4 exceeds 1000 nm, the response time for hydrogen gas detection becomes slowed. If the thickness is less than 5 nm, the strength may be insufficient.

The material of the first ceramic 6 is preferably nitrides or oxides of group IVa, Va, or VIa metal elements. Specific examples of the material of the first ceramic 6 include nitrides such as $TiN_{0.3-2.5}$, $ZrN_{0.3-2.5}$, $HfN_{0.3-2.5}$, $VN_{0.3-2.5}$, $NbN_{0.3-2.5}$, $TaN_{0.8-2}$, $CrN_{0.5-3}$ $MoN_{0.5-3}$, and $WN_{0.5-3}$; and oxides such as $TiO_{0.5-3}$, $ZrO_{1-3}$, $HfO_{1-3}$, $VO_{0.5-3}$, $NbO_{0.5-3}$, $TaO_{1-3}$, $CrO_{0.5-5}$, $MoO_{1-4}$, and $WO_{1-4}$.

Among these, the preferable nitrides include $TaN_{0.8-2}$, $TiN_{0.3-2.5}$, $ZrN_{0.3-2.5}$, $HfN_{0.3-2.5}$, and $WN_{0.5-3}$; and the preferable oxides include $HfO_{1-3}$, $TaO_{1-3}$, and $WO_{1-4}$.

At least one type of metal particle selected from the group consisting of yttrium Y, cerium Ce and lanthanum La is preferably as the rare earth metal particles 8 dispersed in the aforementioned first ceramic 6 in terms of superior hydrogen detection capacity. The rare earth metal particles may be of one type or a mixture multiple types of rare earth metal particles.

The particle size of the rare earth metal particles 8 is preferably 1 to 10 nm, and more preferably 3 to 8 nm; and the particle size is smaller than the thickness of the detection film 4.

The shape of the rare earth metal particles 8 is not particularly limited, and may be spherical, elliptical, rectangular, cylindrical, irregular or the like. The hydrogen detection capacity is improved when using rare earth metal particles 8 that are cylindrical or square rod-shaped, have a large aspect ratio, and are within the stipulated particle size. This is preferable. When particles with a large aspect ratio are used, particularly when dispersed in the first ceramic 6 such that the long axis of the rare earth metal particles 8 are made to align in the thickness direction of the detection film 4, there is a particularly strong effect to improve the hydrogen detection capacity. If cylindrical or square rod-shaped particles are used, that aspect ratio is preferably 1:10, more preferably, 1.5:5.

In the present invention, the thickness of the detection film is preferably determined corresponding to the purpose of use. If the hydrogen gas concentration to be measured is a comparatively low one, for example, 1 volume % or less, specifically, less than 5000 ppm, then the thickness is preferably 100 nm or less, more particularly 50 nm or less, and particularly preferably 40 to 5 nm.

A hydrogen gas leak detector may be cited as an example of a use to detect low concentration hydrogen gas.

If the hydrogen gas concentration to be measured is a comparatively high one, specifically, 5 volume % or more, then the thickness is preferably 100 nm or more, and more preferably 300 to 1000 nm. A hydrogen sensor for controlling the hydrogen gas concentration in a device may be cited as an example of a use to detect this kind of high concentration hydrogen gas.

The content percentage of rare earth metal particles in the detection film 4 is preferably 30 to 70 mass %, and more preferably 40 to 60 mass %. If the content percentage is less than 30 mass %, the sensitivity of the sensor decreases. Meanwhile, if the content percentage exceeds 70 mass %, the volume change of the rare earth metal particles caused by hydrogenation becomes large, inducing notable deterioration of the detection film and the protective film.

(Protective Film)

The hydrogen permeable protective film 10 is laminated on the surface of the aforementioned detection film 4. This protective film 10 has the function of allowing only hydrogen to permeate through the hydrogen permeable metal particles dispersed therein.

The aforementioned hydrogen permeable protective film 10 is composed of a second ceramic 12 to configure a matrix, and the multiple hydrogen permeable metal particles 14 are roughly uniformly dispersed therein.

The thickness of the protective film is preferably 5 to 40 nm, more preferably 7 to 20 nm. If the thickness of the protective film exceeds 40 nm, the response time for hydrogen gas detection becomes slowed. Or, the measurement precision declines. If the thickness is less than 5 nm, the strength may be insufficient. Further, it may not be possible to sufficiently prevent the adverse effects on the detection film by non-hydrogen components such as nitrogen, oxygen, ammonia, and hydrocarbons.

The material of the second ceramic 12 is preferably nitrides or oxides of group IVa, Va, and VIa metal elements. Specific examples of the material of the second ceramic 12 include nitrides such as $TiN_{0.3-2.5}$, $ZrN_{0.3-2.5}$, $HfN_{0.3-2.5}$, $VN_{0.3-2.5}$, $NbN_{0.3-2.5}$, $TaN_{0.8-2}$, $CrN_{0.5-3}$, $MoO_{0.5-3}$, and $WN_{0.5-3}$; and oxides such as $TiO_{0.5-3}$, $ZrO_{1-3}$, $HfO_{1-3}$, $VO_{0.5-3}$, $NbO_{0.5-3}$, $TaO_{1-3}$, $CrO_{0.5-5}$, $MoO_{1-4}$, and $WO_{1-4}$.

Among these, the preferable nitrides include $TaN_{0.8-2}$, $TiN_{0.3-2.5}$, $ZrN_{0.3-2.5}$, $HfN_{0.3-2.5}$, and $WN_{0.5-3}$; and the preferable oxides include $HfO_{1-3}$, $TiO_{0.5-3}$, $TaO_{1-3}$, and $WO_{1-4}$.

At least one type of metal particle selected from the group consisting of palladium (Pd), platinum (Pt), niobium (Nb), vanadium (V), tantalum (Ta) and alloys of these is preferable as the hydrogen permeable metal particles 14 dispersed in the aforementioned second ceramic 12. These are superior in hydrogen permeability capacity.

These hydrogen permeable metal particles 14 may be dispersed in the ceramic material as individual metal element particles, or as the aforementioned alloy particles. The alloys of hydrogen permeable metal may be those long used in conventional hydrogen permeable films. Examples of alloy elements include silver, calcium, iron, copper, vanadium, nickel, titanium, chrome, zirconium and the like. Alloys of these alloy elements and Pd are particularly preferable.

Further, when using Pd as the hydrogen permeable metal, the Pd has a superior capacity to separate between hydrogen gas and other gases, and therefore the protective film may be made notably thin.

The hydrogen permeable metal particles may be a single type or a mixture of multiple types of hydrogen permeable metal particles.

The particle size of the hydrogen permeable metal particles is preferably 1 to 10 nm, and 2 to 6 nm is more preferable. In addition, the particles are smaller than the thickness of the protective film 4.

The content percentage of the hydrogen permeable metal particles 14 in the hydrogen permeable protective film 10 is preferably 20 to 70 mass %, and more preferably 40 to 60 mass %. If this content percentage is less than 20 mass %, the hydrogen permeability declines. Meanwhile, if this content percentage exceeds 70 mass %, the volume changes induced by hydrogenation of the hydrogen permeable metal particles become large, and the detection film 4 and the protective film 10 deteriorate notably. Further, a protective film in which the hydrogen permeable metal particle content percentage exceeds 70 mass % will have insufficient mechanical strength when forming a thin film. For that reason, manufacturing a protective film with a thickness of 5 to 40 nm will be difficult.

The shape of the hydrogen permeable metal particles 14 is not particularly limited, and may be spherical, elliptical, rectangular, cylindrical, irregular or the like. The hydrogen permeation characteristics of the protective film 10 are improved when using hydrogen permeable metal particles 14 that are cylindrical or square rod-shaped and have a large aspect ratio, therefore employing these hydrogen permeable metal particles are preferable. When particles with a large aspect ratio are used, particularly when dispersed in the second ceramic 12 such that the long axis of the rare hydrogen permeable metal particles 14 are made to align in the thickness direction of the protective film 10, there is a particularly strong effect to improve hydrogen permeability. If cylindrical or square rod-shaped particles are used, that aspect ratio is preferably 1 to 10, more preferably, 1.5 to 5.

Figure 2:
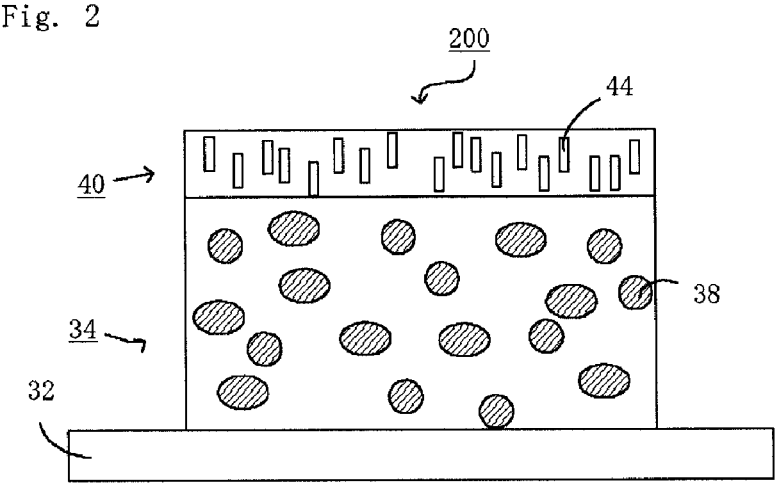
FIG. 2 is a cross-sectional diagram indicating another example of the hydrogen sensor of the present invention.

FIG. 2 is a conceptual diagram indicating another example of a hydrogen sensor of the present invention. In FIG. 2, 200 is a hydrogen sensor, 32 is a substrate, 34 is a detection film, 38 is rare earth metal particles, and 40 is a protective film. Hydrogen permeable metal particles 44 dispersed in the protective film 40 of this sensor 200 are rod-shaped, and are dispersed in the protective film 40 with the long axes of the particles in parallel with the thickness direction of the protective film 40. As previously described, this protective film 40 has superior hydrogen permeability, and as a result, the sensor response speed is high.

Figure 3:
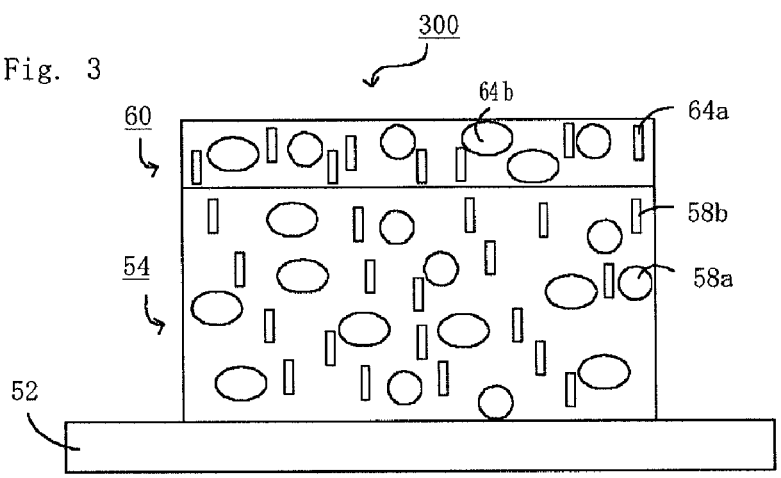
FIG. 3 is a cross-sectional diagram indicating yet another example of the hydrogen sensor of the present invention.

FIG. 3 is a conceptual diagram indicating yet another example of a hydrogen sensor of the present invention. In FIG. 2, 300 is a hydrogen sensor, 52 is a substrate, 54 is a detection film, and 60 is a protective film. Two differing shapes of hydrogen permeable metal particles 64a, 64b are dispersed in the protective film 60 of this sensor 300. The hydrogen permeable metal particles 64a are rod-shaped, and are dispersed in the protective film with the long axes of the particles in parallel with the thickness direction of the protective film 40. The hydrogen permeable metal particles 64b are roughly spherical.

A mixture of rod-shaped rare earth metal particles 58a and roughly spherical rare earth metal particles 58b are dispersed in the detection film 54 in the same way. Further, the rod-shaped rare earth metal particles 58a are aligned in the thickness direction of the detection film 54, and are oriented in the long axis direction.

Figure 4:
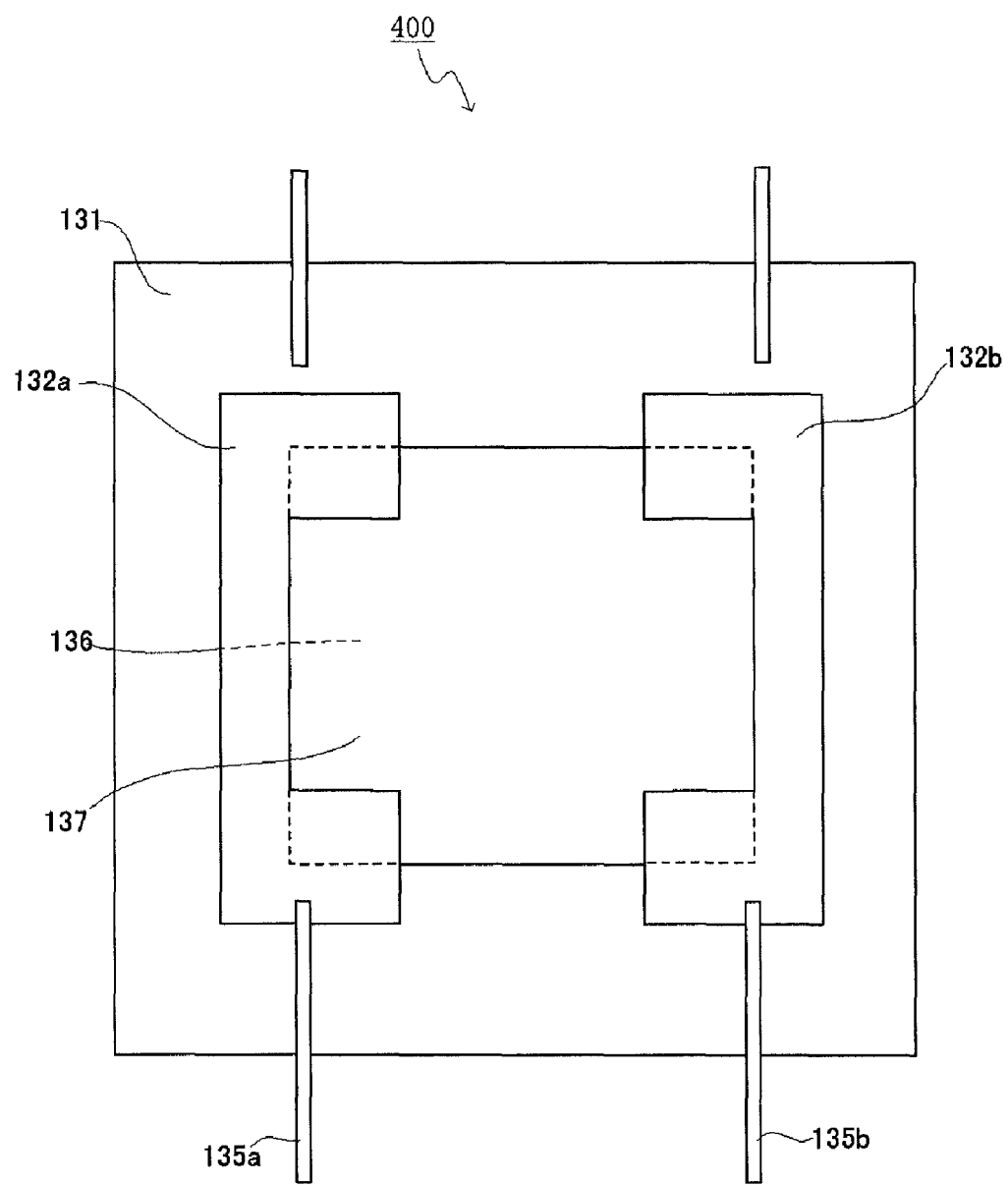
FIG. 4 is a top view diagram indicating one example of the hydrogen sensor element unit incorporating the hydrogen sensor of the present invention.

FIG. 4 is a top view diagram indicating one example of a hydrogen sensor element 400 used in a hydrogen sensor of the present invention. In FIG. 4, 131 is a substrate. A pair of element electrodes 132a, 132b are formed mutually opposite each other on the substrate 131. 135a, 135b are sensor signal take-off wires, and are connected to the aforementioned element electrodes 132a, 132b. 136 is a detection film. 137 is a protective film and is formed to completely cover the upper surface of the aforementioned detection film 136. Consequently, the detection film 136 is indicated by the dotted line in FIG. 4.

Figure 5:
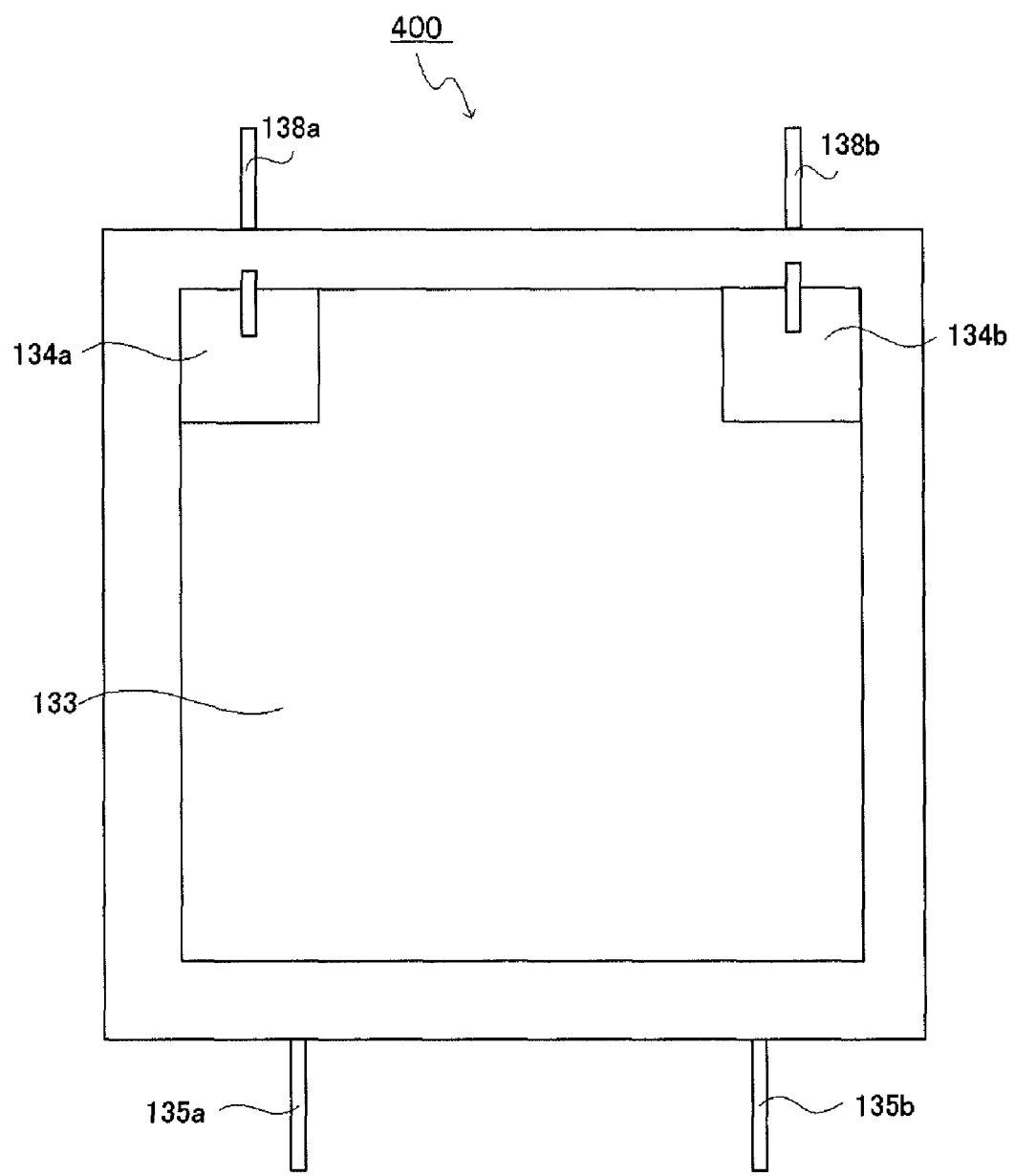
FIG. 5 is a back surface diagram of the hydrogen sensor element unit of FIG. 4.

FIG. 5 is a back surface diagram of the hydrogen sensor element 400 of FIG. 4. In FIG. 5, 133 is a heater formed using a metal resistor, and is formed on the back surface of the substrate 131. 134a, 134b are heater electrodes, and are connected to the aforementioned heater 133. 138a, 138b are wiring to supply power for heating the aforementioned heater 133.

Figure 6:
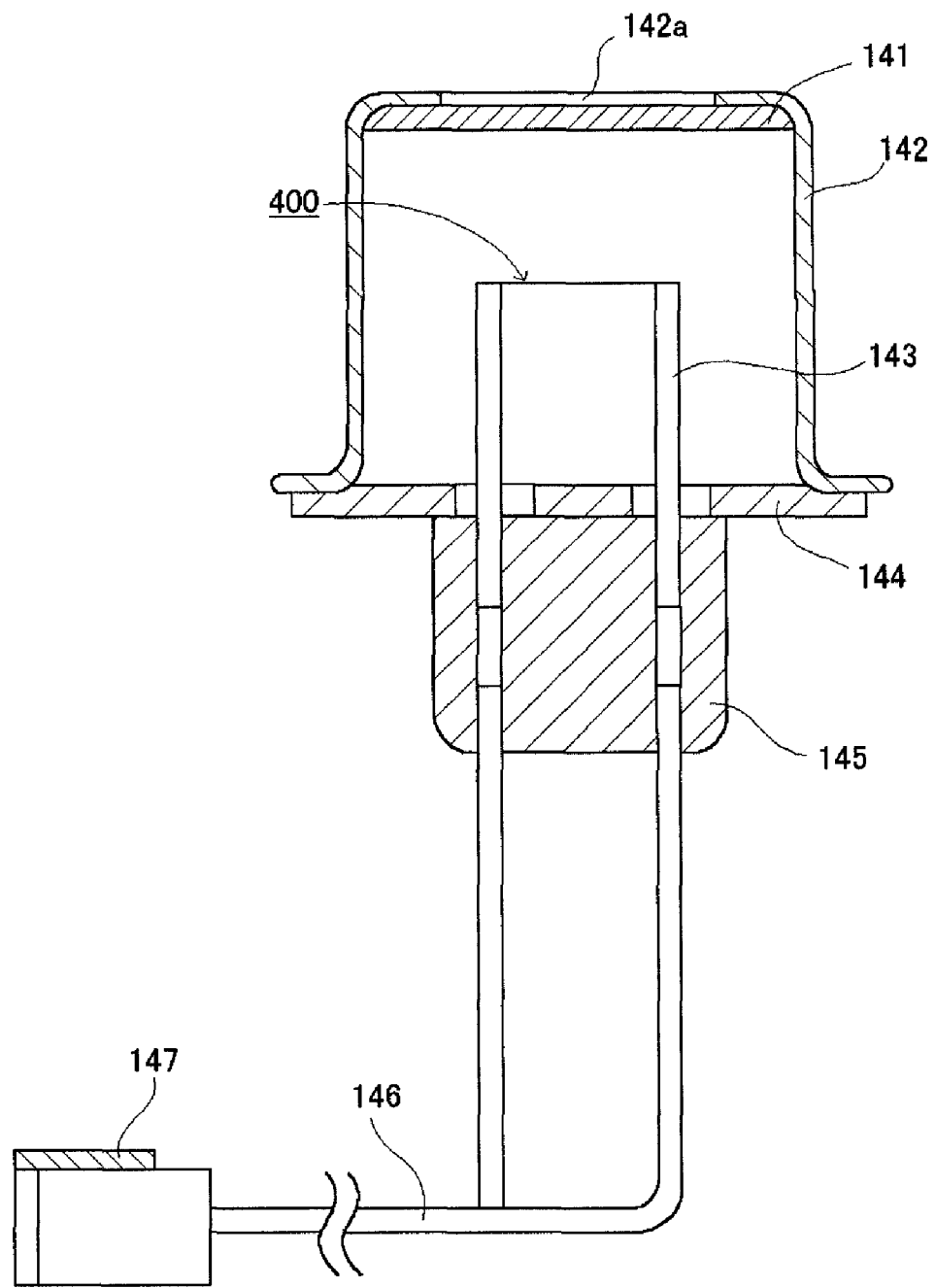
FIG. 6 is a cross-section diagram indicating one example of a sensor unit incorporating the hydrogen sensor of the present invention.

FIG. 6 is a cross-section diagram indicating one example of a sensor unit incorporating the hydrogen sensor 400 of the present invention. In FIG. 6, 142 is a cylindrical cap having a bottom, 141 is a filter installed in the cap 142, through which hydrogen passes, and 142a is a ventilation port formed in the bottom of the cap 142.

Atmospheric gas, such as outside air containing hydrogen, passes through this ventilation port 142a, disperses within the filter 141, and arrives at the hydrogen sensor 400 where the hydrogen concentration is detected. 143 is a pin that supports the hydrogen sensor 400, 144 is a plate, 145 is a grommet, 146 is a cord, and 147 is a connector. Heating power is supplied to the heater (not indicated in the diagram) of the hydrogen sensor 400 through the connector 147, the cord 146 and the pin 143, and the output of the hydrogen sensor 400 is also taken out through these.

Figure 7:
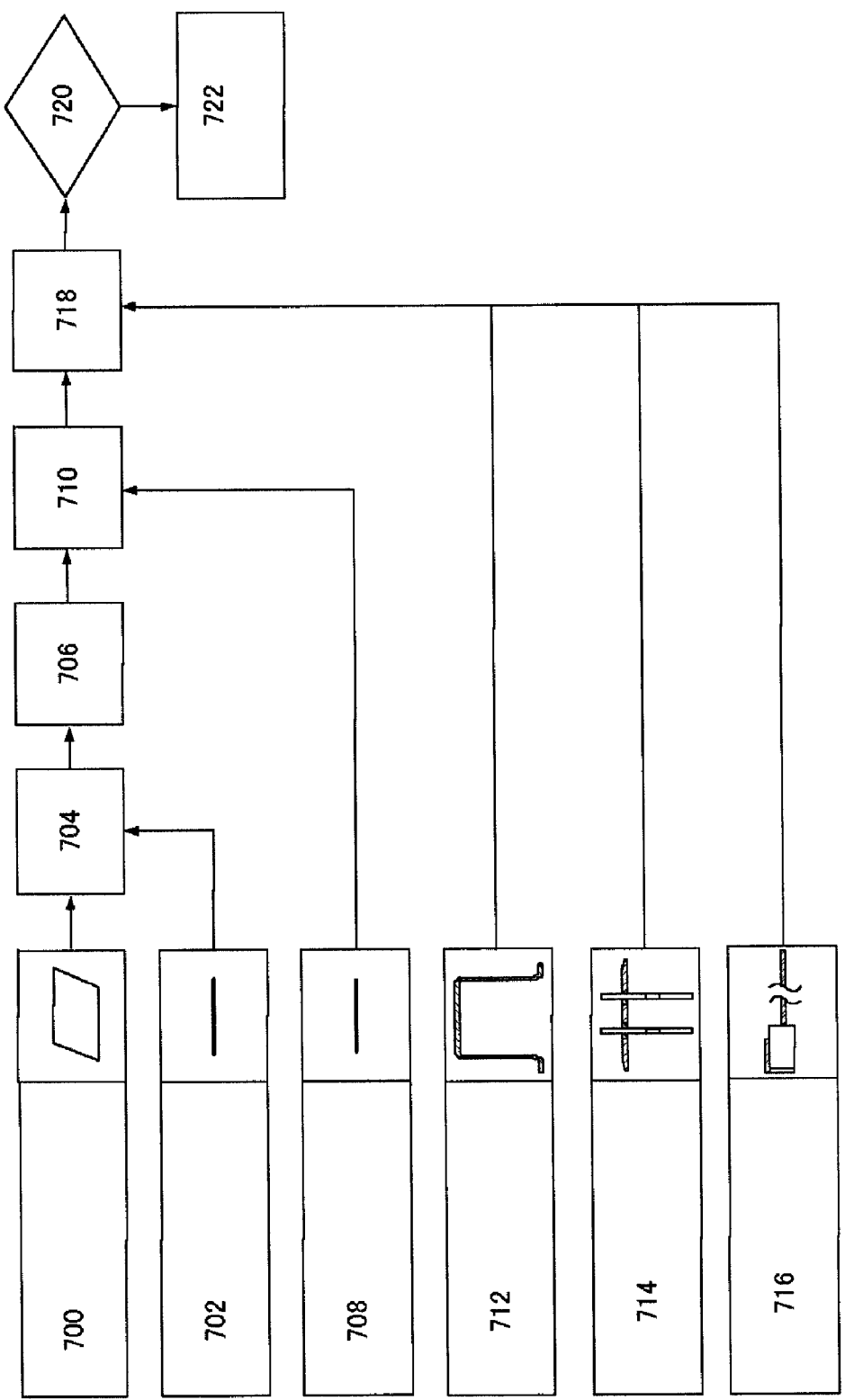
FIG. 7 is a processing diagram indicating one example of the manufacturing flow of a hydrogen sensor of the present invention.

FIG. 7 is a processing diagram indicating one example of the manufacturing method of a hydrogen sensor of the present invention. First, a heater electrode pattern 702 is printed 704 on a substrate 700 using a resistive paste containing platinum or the like, and a thick film heater is formed by sintering 706 this.

The heater is preferably a thick film resistor formed in a specified pattern on the surface of the substrate in a thick film of platinum, ruthenium oxide, silver-platinum alloy or the like.

Next, in order to form electrodes for the heater, electrode patterns are printed using gold paste or the like, and this is sintered. Element electrode patterns are printed in the same way using gold paste, and are sintered to provide a substrate for manufacturing a hydrogen sensor. A hydrogen sensor is obtained by forming 710 the detection film and protective film 708 on this substrate for a hydrogen sensor.

A hydrogen sensor unit is manufactured by incorporating 718 a cap 712, plate 714, cord 716, etc. onto the hydrogen sensor obtained. The manufactured hydrogen sensor unit is submitted to quality inspection 720 as necessary, and if there are no quality problems, is commercialized as hydrogen sensor unit 722.

Figure 8:
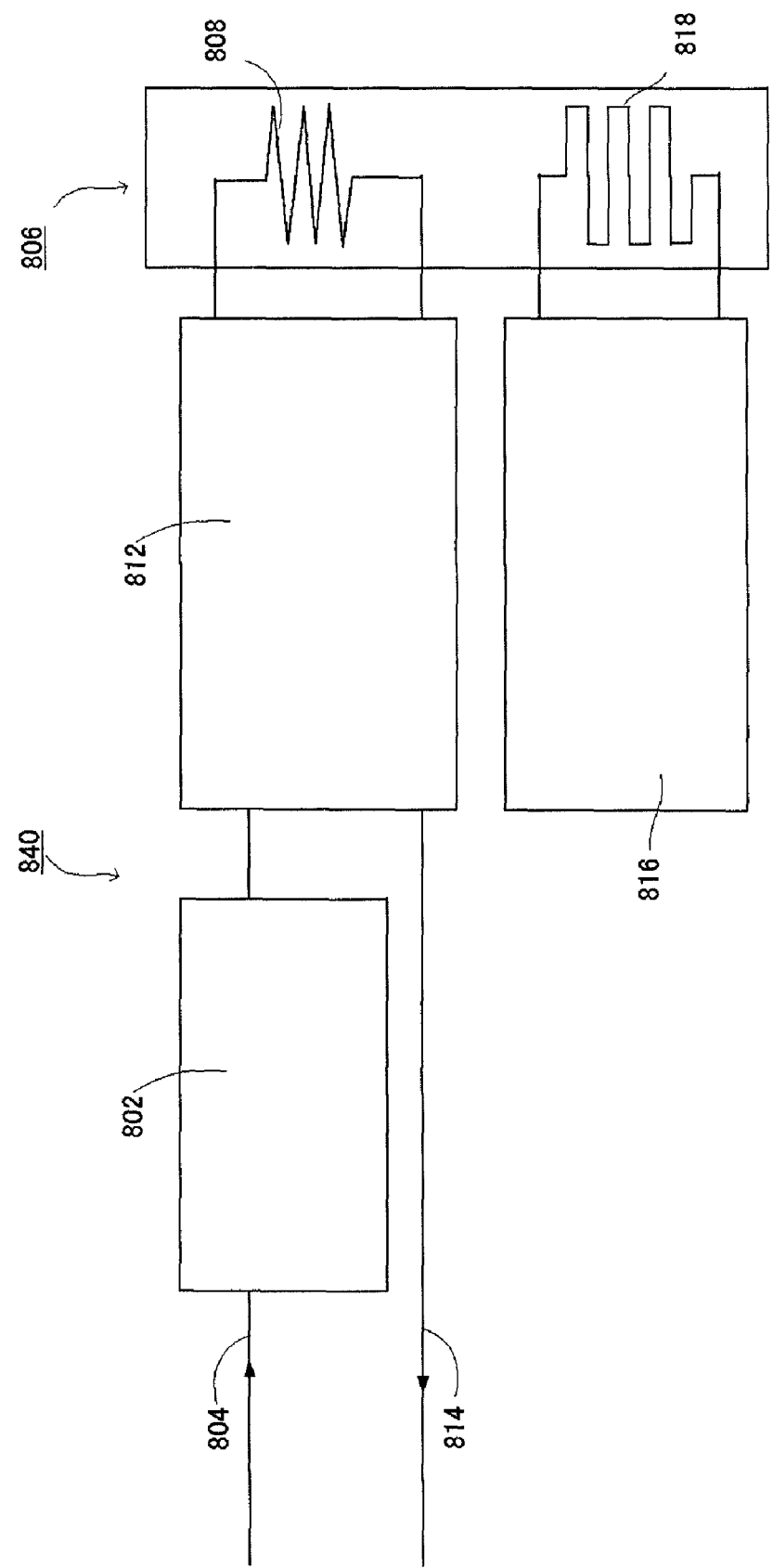
FIG. 8 is a block diagram indicating one example of a control unit that controls the signals and heater temperature of a hydrogen sensor of the present invention.

FIG. 8 is a block diagram indicating one example of a control unit that controls the signals and heater temperature of a hydrogen sensor of the present invention. At control unit 840, current 804 supplied from a power source not indicated in the diagram is converted to constant current by a power source circuit and a standard current generation circuit 802, and is sent to a hydrogen sensor element unit 806. The resistance change and voltage change of the hydrogen sensor produced by a hydrogen sensor 808 within the hydrogen sensor element unit detecting hydrogen gas is sent to a sensor signal processing circuit 812. Here, after signal processing to correct the output by converting the resistance value of the sensor to voltage, this signal is taken off from the signal processing circuit 812 as sensor output 814 (hydrogen gas concentration measured value). Meanwhile, a temperature control circuit 816 controls the output of the heater 818 so that the hydrogen sensor becomes the specified set temperature.

Figure 9:
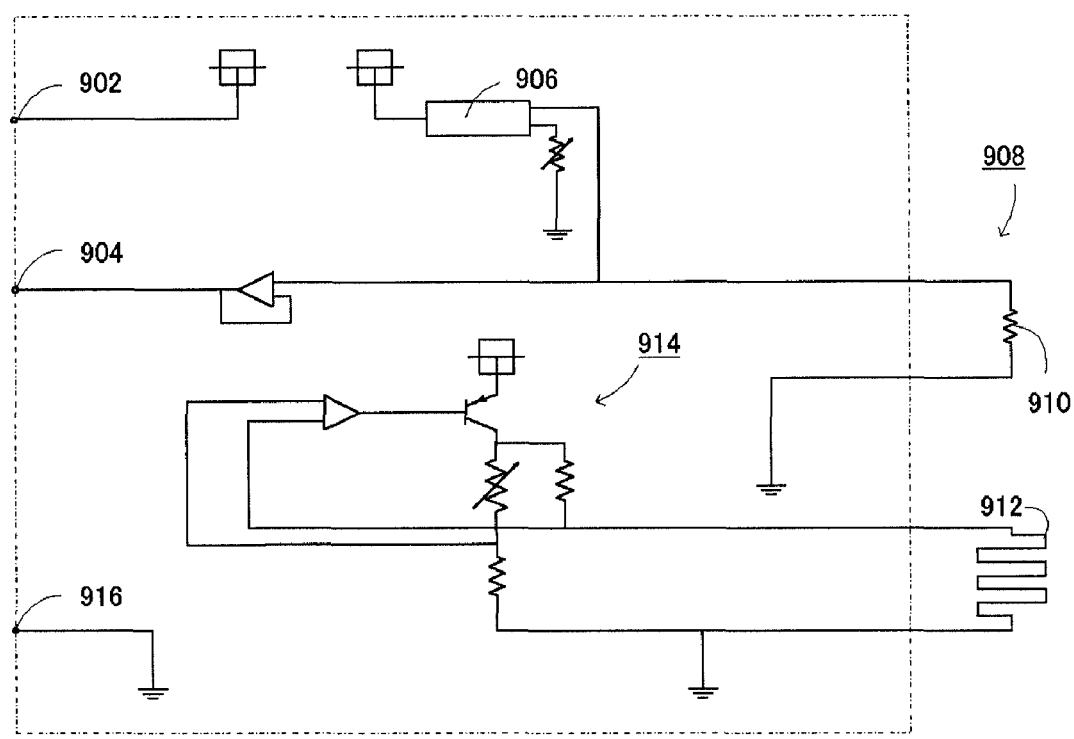
FIG. 9 is a circuit diagram indicating one example of a control unit that controls the signals and heater temperature of a hydrogen sensor of the present invention.

FIG. 9 is a circuit diagram indicating one example of a control unit that controls the signals and heater temperature of a hydrogen sensor. In this circuit, the hydrogen concentration measured value explained using FIG. 8 is taken of as the sensor output. Moreover, the temperature of the hydrogen sensor explained using FIG. 8 is controlled by a heater output adjustment circuit.

In FIG. 9, 902 is a power source terminal, 904 is a sensor output terminal, 906 is a constant current circuit, 908 is a hydrogen sensor element unit, 910 is a hydrogen sensor, 912 is a heater, 914 is a heater output adjustment circuit, and 916 is an earth terminal.

(Manufacturing Method of a Hydrogen Sensor)

The hydrogen sensor of the present invention is preferably manufactured by the following method. First, a detection film is formed by vapor phase epitaxy or sputtering on at least one surface of the substrate. Next, A protective film is formed on the detection film by vapor phase epitaxy or sputtering.

For example, the detection film can be formed on the substrate by conducting simultaneous vapor phase epitaxy of a rare earth metal and the first ceramic material onto the substrate in a vacuum atmosphere, or this may be done by sputtering in an argon atmosphere. The content percentage of rare earth metal particles in the detection film can be controlled by the following methods.

(1) Modify the output of the rare earth metal target. Modify the output of the ceramic material target. Or, modify both target outputs.

(2) Modify the compounding percentages of rare earth metal and ceramic material in a mixed target.

(3) Change the surface areas of the ceramic targets using a complex target in which a small volume planar rare earth metal target is arranged on the surface of the ceramic target. In the case of a magnetron sputtering device, arrange in the magnetic field of the magnet positioned by the cathode.

Reactive sputtering using a nitrogen gas or oxygen gas atmosphere can not be adopted. If reactive sputtering is adopted, a corresponding rare earth compound is produced, and the hydrogen gas detection capability is lost.

The protective film is obtained by simultaneously sputtering a hydrogen permeable metal element and a ceramic material to form the protective film on the detection film. The same methods used to control the aforementioned content percentage of rare earth metal particles can be adopted for controlling the content percentage of the hydrogen permeable metal particles in the protective film.

The hydrogen permeable metal particles and the rare earth metal particles provided by this kind of method are mixtures of ordinary roughly spherical particles and rod shaped particles. Reactive sputtering may be adopted to manufacture the protective film.

EXAMPLES

Next, the present invention will be concretely explained by using examples, but the present invention is not limited to these examples.

Example 1

The hydrogen sensor indicated in FIG. 1 was formed onto a glass substrate using a high frequency magnetron sputtering device.

First, glass substrate, Y target and TaN target was arranged in the high frequency magnetron sputtering device, and the pressure was reduced to about $4 \times 10^{-5}$ Pa in the device. Next, argon gas was introduced into the device ($9.3 \times 10^{-1}$ Pa), and the sputtering was conducted for 1 minute at room temperature. As a result, a 70-nm thick layer of TaN—Y thin film (detection film with Y particles diffused in TaN ceramic) was formed on the glass.

The mean particle size of the Y metal particles in the detection film was 4 nm, and the content percentage was 45 mass %. It was confirmed that the shape of the Y metal particles was a roughly 2:3 mixture of rod-shaped and spherical particles.

Further, to observe the shape of the Y metal particles in the TaN—Y thin film, the temperature of an Si substrate was maintained at room temperature, a film was formed on the Si substrate by the same operations as when forming the detection film, and this film was observed by transmission electron microscope.

Next, using Pd and Ta targets, argon gas and nitrogen gas (volume ratio 85:15 Pa) were introduced into the device, the substrate temperature was held at room temperature at a pressure of $9.3 \times 10^{-1}$ Pa, and reactive sputtering was conducted for 4 minutes. As a result, a protective film 20 nm thick was formed on the detection film. The protective film formed had Pd with a particle size of 2 to 6 nm uniformly dispersed in TaN ceramic. The Pd content in the protective film was 45 mass %.

Subsequently, electrodes were formed by sputtering a film of Au 200 nm thick. Further, a heater as formed on the back side of the substrate, thus yielding a hydrogen sensor.

This hydrogen sensor was incorporated into the hydrogen sensor unit indicated in FIG. 6. The concentration of hydrogen in a mixed gas (mixed with nitrogen gas) was measured using this unit. The hydrogen concentration in the mixed gas was varied in the range of 0 to 4000 ppm.

Figure 10:
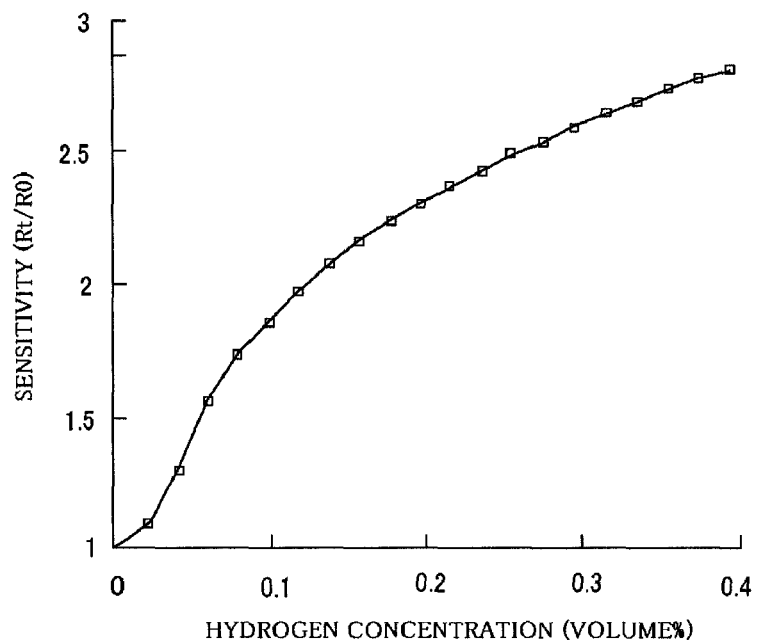
FIG. 10 is a graph indicating one example of the relationship between the hydrogen gas concentration and the sensitivity of the hydrogen sensor of the present invention.

FIG. 10 is a graph indicating the correlation between the hydrogen gas concentration and the sensitivity when measured using the aforementioned hydrogen sensor.

Sensitivity is defined using the following formula.

Sensitivity=element resistance value (Rt) at the measured hydrogen concentration/the element resistance value (R0) at hydrogen concentration 0

While maintaining the element temperature at 150° C., the hydrogen gas concentration was varied from 200 ppm to 4000 ppm in 200 ppm increments. The result is such that the changes in resistance value Rt were observed from 200 ppm, and the increase in Rt was observed according to the increase in concentration until 4000 ppm.

The hydrogen sensor of Example 1 accurately detected hydrogen gas at a low concentration of less than 5000 ppm, which is required for detection of hydrogen gas leaks. Consequently, it was confirmed that this hydrogen sensor is suitable for detecting low concentration hydrogen gas leaks.

(Durability Testing)

Figure 11:
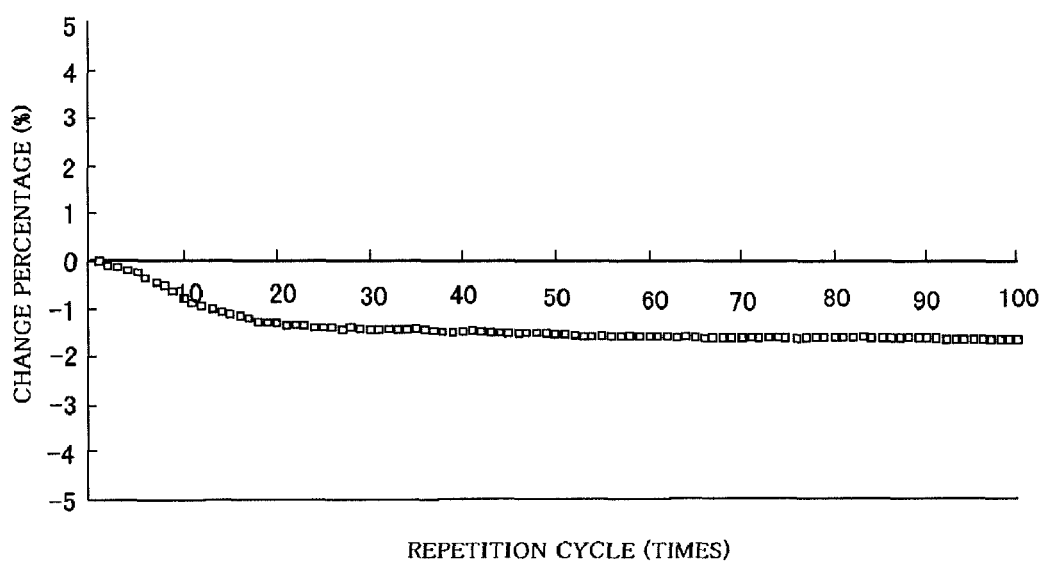
FIG. 11 is a graph indicating the results of testing the durability of the hydrogen sensor indicated in FIG. 10.

The hydrogen sensor manufactured in Example 1 was maintained at 150° C., and in this state was alternatively exposed to air (hydrogen concentration 0 volume %, 15 minutes) and hydrogen concentration 1 volume % (10 minutes) 100 times. The results are indicated in FIG. 11.

The change in sensor output after exposure 100 times was within 2% when comparing the initial value as basis. It was confirmed from these results that the sensor of Example 1 has sufficient durability.

Further, the thicknesses of the rare earth metal film and of the protective film were measured by stylus surface profiler, and the composition was measured by EPMA (electron probe micro-analyzer).

Example 2

Y and HfO were simultaneously sputtered on a glass substrate, and a 70-nm thick detection film was formed with Y particles dispersed in HfO ceramic. Next, a 20-nm thick protective film with Pd particles dispersed in HfO ceramic was formed on the aforementioned detection film by simultaneous sputtering using Pd and HfO targets. Au electrodes were formed in the same manner as in Example 1, and a sensor element was obtained.

Figure 12:
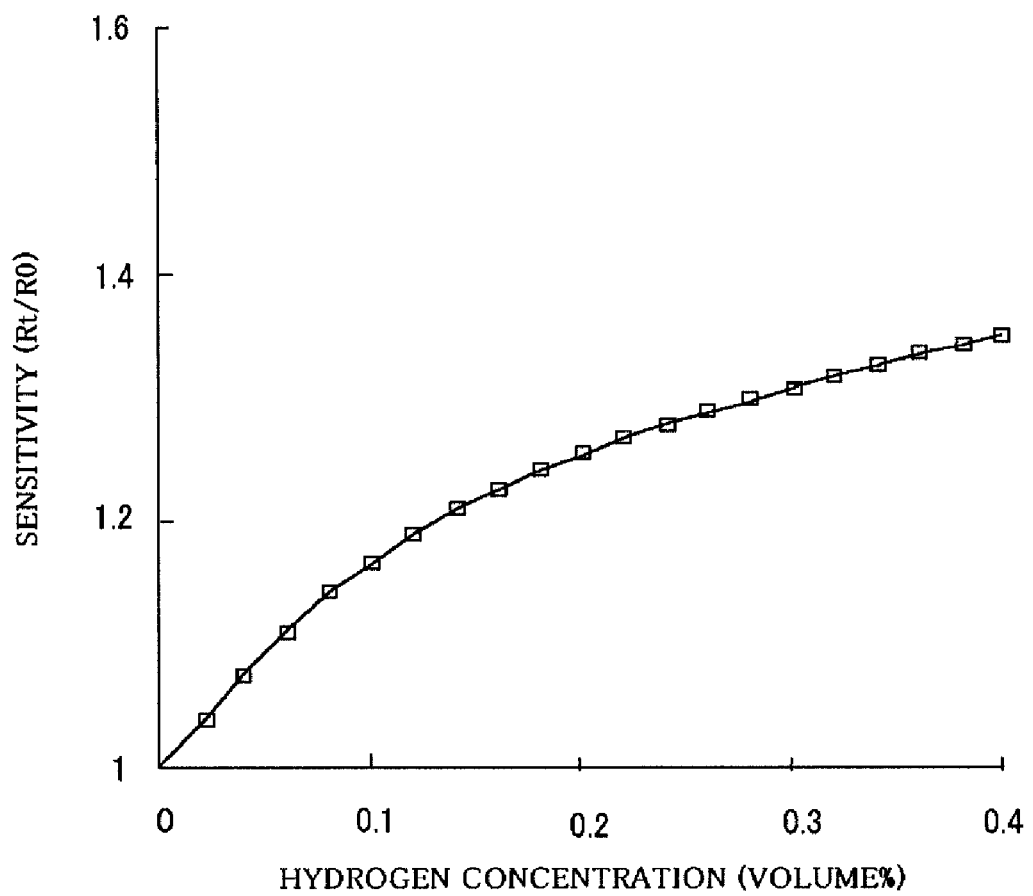
FIG. 12 is a graph indicating another example of the relationship between the hydrogen gas concentration and the sensitivity of the hydrogen sensor of the present invention.

The relationship between the hydrogen concentration and the sensitivity of this sensor element was investigated. The results are indicated in FIG. 12.

The invention claimed is:

1. A hydrogen sensor comprising a substrate, a detection film formed on said substrate, and a hydrogen permeable protective film formed on said detection film, wherein said detection film comprises a first ceramic and rare earth metal particles dispersed in said first ceramic, and said protective film comprises a second ceramic and hydrogen permeable metal particles dispersed in said second ceramic.

2. The hydrogen sensor according to claim 1, wherein the thickness of the detection film is 5 to 1000 nm, and the thickness of the hydrogen permeable protective film is 5 to 40 nm.

3. The hydrogen sensor according to claim 1, wherein the detection film contains 30 to 80 mass % rare earth metal particles.

4. The hydrogen sensor according to claim 1, wherein the rare earth metal particles are formed of at least one selected from the group consisting of yttrium (Y), cerium (Ce) and lanthanum (La).

5. The hydrogen sensor according to claim 1, wherein the rare earth metal particles are amorphous particles or rod-shaped particles.

6. The hydrogen sensor according to claim 1, wherein the first ceramic of the detection film is formed of a nitride or oxide of group IVa, Va or VIa metal elements.

7. The hydrogen sensor according to claim 1, wherein the content percentage of the hydrogen permeable metal particles in the hydrogen permeable protective film is 20 to 70 mass %.

8. The hydrogen sensor according to claim 1, wherein the hydrogen permeable metal particles are amorphous particles or rod-shaped particles.

9. The hydrogen sensor according to claim 1, wherein the hydrogen permeable metal particles are at least one selected from the group consisting of palladium (Pd), platinum (Pt), niobium (Nb), vanadium (V), tantalum (Ta) and alloys of these.

10. The hydrogen sensor according to claim 1, wherein the second ceramic of the hydrogen permeable protective film is formed of a nitride or oxide of group IVa, Va or VIa metal elements.

11. The hydrogen sensor according to claim 1, wherein the ceramics forming the detection film and the hydrogen permeable protective film are formed of the same materials.

12. The hydrogen sensor according to claim 1, wherein the substrate is a glass plate or a ceramic plate.

13. The hydrogen sensor according to claim 1, wherein a heater is provided on the substrate.

14. The hydrogen sensor according to claim 12, wherein the heater is a resistance film which is formed on one surface of the substrate and formed of platinum, ruthenium oxide or silver-palladium alloy film.

15. A method for manufacturing the hydrogen sensor described in claim 1, wherein a detection film in which rare earth metal particles are dispersed in a first ceramic is formed by conducting vapor phase epitaxy or sputtering of a rare earth metal and the first ceramic material simultaneously onto one side of a substrate, and then a protective film in which hydrogen permeable metal particles are dispersed in a second ceramic is formed by conducting vapor phase epitaxy or sputtering of a hydrogen permeable metal and the second ceramic material simultaneously onto said detection film.

16. The method for manufacturing the hydrogen sensor according to claim 15, wherein the rare earth metal particles or hydrogen permeable metal particles are amorphous particles or rod-shaped particles.

* * * * *